United States Patent
Spitz et al.

(10) Patent No.: US 6,849,236 B2
(45) Date of Patent: Feb. 1, 2005

(54) ANALYZER SYSTEM FOR LID-COVERED SAMPLE CONTAINERS

(75) Inventors: Urs Spitz, Herrliberg (CH); Albert Aichert, Oberdürnten (CH); Willi Wälte, St. Margrethen (CH)

(73) Assignee: Mettler-Toledo GmbH, Greifensee (CH)

(*) Notice: Subject to any disclaimer, the term of this patent is extended or adjusted under 35 U.S.C. 154(b) by 390 days.

(21) Appl. No.: 09/972,160

(22) Filed: Oct. 5, 2001

(65) Prior Publication Data

US 2002/0041828 A1 Apr. 11, 2002

(30) Foreign Application Priority Data

Oct. 6, 2000 (DE) .......................................... 100 49 491

(51) Int. Cl.[7] ............................................... G01N 33/00
(52) U.S. Cl. ............................. 422/62; 422/63; 422/64; 422/68.1; 422/104; 436/43; 436/47; 435/305.3; 435/305.4
(58) Field of Search ........................... 422/62–64, 68.1, 422/104; 436/43, 45, 47, 48–49; 435/305.3, 305.4

(56) References Cited

U.S. PATENT DOCUMENTS

| | | | |
|---|---|---|---|
| 4,455,280 A | 6/1984 | Shinohara et al. | |
| 4,535,585 A | 8/1985 | Gardos | |
| 5,628,962 A | 5/1997 | Kanbara et al. | |

OTHER PUBLICATIONS

Patent Abstracts of Japan, JP 07020132, Jan. 24, 1995.

*Primary Examiner*—Lyle A. Alexander
(74) *Attorney, Agent, or Firm*—Friedrich Kueffner

(57) ABSTRACT

An analyzer system has a base housing (1) and a sample tray (4) with at least two holding accommodations (5) for containers (32) of samples that are to be analyzed. The sample tray (4) is movably supported on the base housing. A drive mechanism (2) inside the base housing advances the tray (4) so that the containers (32) move in steps along a prescribed track to an analyzer module (16), where the samples are subjected to an analysis. A lid-opening device (50) is arranged along the prescribed track at a place that the sample containers (32) reach before they arrive at the analyzer module (16). The lid-opening device (50) serves to open lids (32') of a predetermined shape and thickness (H) by which the sample containers (32) may be covered. The lids (32') are preferably made of a non-magnetic material containing a magnet-anchor element.

18 Claims, 2 Drawing Sheets

ANALYZER SYSTEM FOR LID-COVERED SAMPLE CONTAINERS

BACKGROUND AND SUMMARY OF THE INVENTION

The invention relates to an analyzer system with a base housing containing a drive mechanism for a sample tray. The sample tray has at least two holding accommodations for samples that are in the process of being analyzed. The drive mechanism advances the sample tray in a stepwise motion so that the samples in the holding accommodations are transported along a prescribed track to an analyzer module that is attached to the base housing of the analyzer system. The invention further relates to an at least partially magnetic lid for covering a sample that is to be processed by the inventive analyzer system. An analyzer system of the kind that the invention relates to is known from the German patent application DE 100 18 876.1 which has not been published.

The primary focus in the aforementioned earlier patent application is on automation and efficiency improvements in an analytical process. In addition to being performed in a fast and effective way, an analysis generally has to be free of errors caused by evaporation of volatile components of a test sample.

The object of the present invention is to provide a means for protecting the sample from contamination from the outside and for preventing evaporation of the sample, e.g., in case the analyzer system is stopped temporarily. Vapors escaping from the sample are particularly undesirable if they are malodorous such as ammonia or sulfur compounds, e.g. mercaptans, etc.

According to the present invention, the foregoing objective is accomplished if an analyzer system of the kind described above is equipped with a device for opening lids of a given shape and thickness that may cover the samples. The lid-opener device is arranged at a location along the sample track upstream of the analyzer module. One difficulty encountered in solving the given task was that while it is well known to cover a sample with a lid when this is deemed necessary, a lid will block the access to the sample that is to be processed by the analyzer system. The solution proposed by the present invention makes it possible to uncover the sample without thereby interfering with the automatic analysis of the sample.

Lid-handling arrangements of various configurations are known in other applications, namely in storing, transporting and handling of bulk materials. For example in GB-A-1 380 067, in the context of FIG. 4, a mechanical lid-opening and -holding arrangement is described, albeit without giving any indication of how the device cooperates with the lid. An idea of how a lid-handling device could interact mechanically with a lid to lift the latter off a sample is given in EP-A-0 847 946. Another solution, where the lid is moved sideways, is described in FR-A 2 640 598. As an example of a non-mechanical lid-handling device, EP-A-0 547 861 proposes a suction cup for grasping a smooth lid surface. Finally, a magnetic lid-handling device has become known from DE-C-1 188 882.

All of the aforementioned known lid-opening/holding devices are intended for designs of a coarser dimensional scale. Thus, they involve relatively complex arrangements that are not adaptable for the purposes of an analyzer system. However, it should be noted that within the scope of the invention, mechanical as well as pneumatic solutions could also be used. In particular, an analyzer system according to the invention does not necessarily have to include a lid-holding device. As an example, the lid could be attached to the sample container through a hinge. As the container approaches the analyzer module, the lid is turned up, and after the analysis has been completed, the lid is turned down again by a separate lid-closing device (or it may be closed in some other way).

The concept just outlined would require two separate devices for opening and closing, respectively. It is therefore preferred if the lid-opening device is designed to also work as a lid-holding device to hold the lid during the time when the sample container is open.

As mentioned above, it is also possible under the scope of the invention to use mechanical or pneumatic devices (e.g., suction cups). However, the above-cited references demonstrate how complex such devices can get, particularly if they have to be accommodated in the confined space available in an analyzer system. It is therefore preferred if the lid-holder device has an electromagnet whose excitation current can be turned on and off by a switch.

The magnet in the lid-holder device could for example be designed to be switchable between two operating modes, so that the lid would be attracted in one operating mode to uncover the sample and repelled in a second operating mode to cover the sample again. This would however require an expensive switching arrangement and reversible electromagnets. In comparison, the lid-holder device will be less complicated if the electromagnet has a core of soft iron, so that the remanent magnetization is insignificant after the excitation current has been turned off and the lid is simply released by the magnet.

In principle, a single magnet pole would be sufficient to attract the lid. However, the hold on the lid will be particularly secure if the electromagnet is configured with a yoke, i.e., a U-shaped core with the two poles facing the lid, because this arrangement allows the magnetic flux to run in a closed circle with the lid making the connection from one pole to the other.

A magnet can be used in various different ways in the lid-opening/holding device. For example, the magnet could be moved towards the lid, so as to move the lid sideways, or to lift the lid, or to turn up a hinged lid in order to open the sample container. However, a less complicated design is achieved if the electromagnet is arranged at a stationary location above the sample track and at an appropriate height to allow the sample to pass below the magnet, so that the latter simply lifts the lid off the sample.

In order to prevent a situation where the movement of samples could be obstructed because two lids are caught in a position on top of each other as a result of a malfunction (failure to lift off the lid, or current failure in the electromagnet), the arrangement of the lid-opening device, specifically of the electromagnet, is designed with a clear distance of at least twice the lid thickness above the height of a lid-covered sample. This also provides a good level of safety, so that a possible remanent magnetization will not accidentally open a lid, as could occur if the electromagnet and the lid came too close to each other.

In order to allow existing analyzer systems to be modified or retrofitted, it is preferred if the lid-opening device can be mounted on the base housing with a non-destructively releasable mounting arrangement consisting of at least two parts.

It is assumed to be advantageous if the drive mechanism is designed as a rotary drive mechanism for a disk-shaped sample tray, so that the samples move along a circular path, adjacent to which the lid-opening device is installed.

Especially in the latter case (but also with a linear movement of the samples, which is not excluded under the invention) it is advantageous if the sample movement in the analyzer system is run by a program-operated controller unit, where the program includes the actuating steps of a lid-opening/holding device so that lids that may be used on the samples can be taken off and held during the time in which the sample is analyzed, whereupon the device will put the lid back on the sample. With this arrangement, it is practical to design the program so that after removing the lid, the sample is moved to the analyzer module, and following the analysis of the sample, the latter is moved back to the lid-opening/holding device in order to put the lid back on.

An analyzer system according to the invention can be populated with samples with and without a lid for the simple reason that if a sample has no lid, the electromagnet will have nothing to pick up. As another possibility, conditioning vessels could be placed between some or all of the samples, e.g., for the conditioning of the analytical electrodes, or as rinsing/washing containers for the cleaning of analytical devices (pipettes, electrodes, suction orifices, etc.). As a simple way of entering a signal into the analyzer system when a container is not a sample container, it is advantageous if the control arrangement for moving the samples includes at least one sensor mark on the sample tray of the analyzer system and at least one stationary reader device for the sensor mark. The reader device may be installed on the base housing and/or on the analyzer module. Providing a sensor mark and a reader device is in itself an advantageous feature. In addition, it could also possibly be used to control the lid-opening device. As an alternative or in addition, the control arrangement can be connected to a keypad, by which information about the samples and other containers can be entered. Preferably, the keypad is connected to the base housing, in particular through a fixed attachment.

According to the invention, a lid for samples that are processed in the analyzer system is preferably made of a non-magnetic material with an imbedded magnet-anchor element. At least theoretically, it would be conceivable to make the lid entirely of a magnetizable material, but this has proven to be disadvantageous for a variety of reasons. The magnet-anchor element can be set back from the topside of the lid behind a spacer arrangement, e.g., an arrangement of projections or a single projection in the topside of the lid. The spacer arrangement could consist of a magnetizable material bearing against a non-magnetic part of the lid-opening device, or it could consist of a non-magnetic material bearing against any portion of the lid-opening device. This measure assures that the magnet-anchor element cannot come so close to the magnet that the least amount of remanent magnetism could continue to keep the lid stuck to the magnet even after the magnetic hold has been released.

The simplest way of realizing a spacer arrangement is to cover the magnet-anchor element with a layer of non-magnetic material whose thickness defines a predetermined distance by which the magnet-anchor element will be separated from any parts of the lid-opening device. In principle, the magnet-anchor element could simply be placed behind the non-magnetic topside of the lid. However, considering that some samples may give off aggressive vapors, it is more advantageous if the magnet-anchor element is contained within the non-magnetic material of the lid and thereby covered towards the topside as well as towards the sample.

The simplest design within the scope of this inventive concept is to make the lid of a polymer material and to surround the magnet-anchor element with the polymer material, in particular by using an injection-molding process during which the magnet-anchor element is imbedded in the lid.

Particularly in cases as just described, the magnet-anchor element could conceivably be designed as a magnetizable powder that is integrated into the material of the lid. It would also be conceivable to use a simple magnetic plate. However, the magnetic flux lines will take on a more favorable pattern, if the magnet-anchor element is configured as a ring-shaped metal part, preferably of a diameter approximately commensurate with the pole distance of the electromagnet of the lid-opening device.

Particular attention must of course be paid to functional reliability. If the magnet-anchor element is arranged to one side of the lid, the hold between the electromagnet and the magnet-anchor element is less secure and could accidentally break loose because the upward- and downward-directed forces acting on the lid are not in line with each other. If the magnet-anchor element is constituted by several pieces, e.g., distributed over the circumference of the lid, magnetic adhesion is improved and the lid is held more securely, but the lid-opening device becomes more complex. It is therefore preferred if the magnet-anchor element is arranged in a substantially centered position on the lid, whereby all of the aforementioned problems are avoided.

Further details of the invention may be learned from the following description of a preferred embodiment that is represented schematically in the drawings.

DETAILED DESCRIPTION OF A PREFERRED EMBODIMENT

Figure 1:
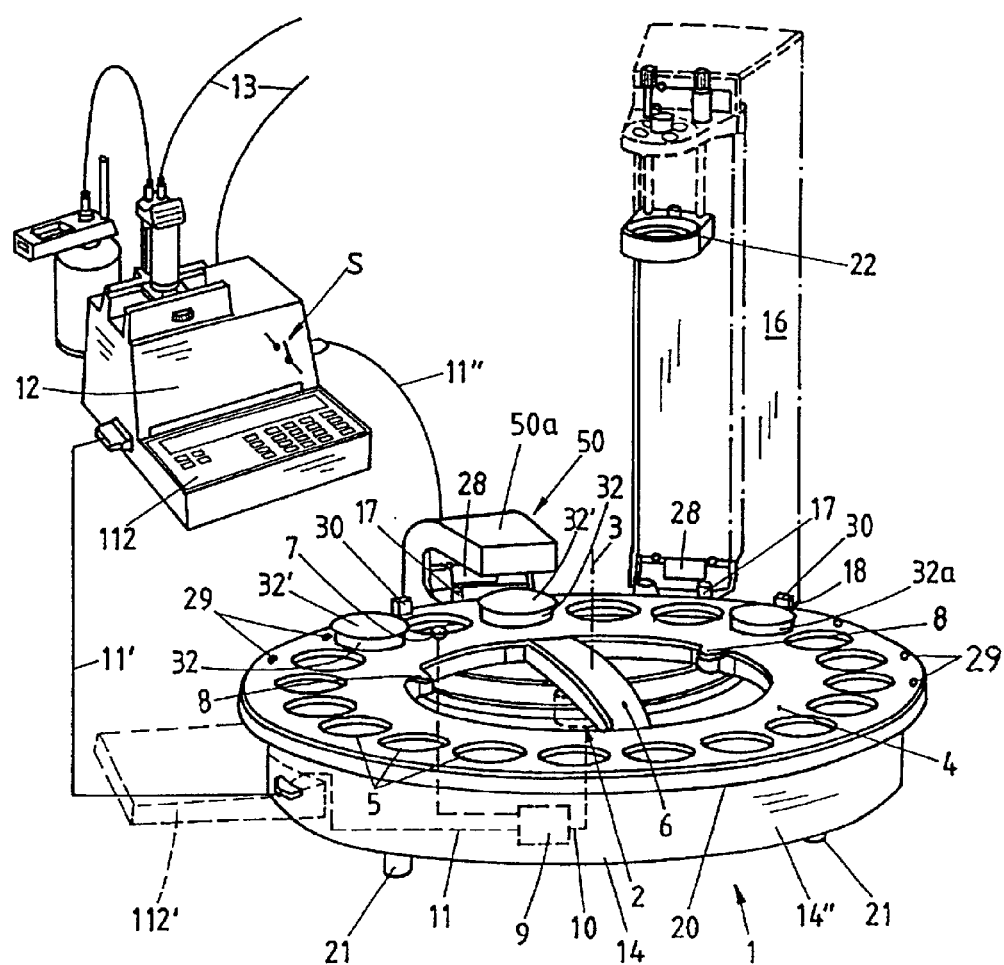
FIG. 1 represents a perspective view of an analyzer system designed according to the invention.

FIG. 1 illustrates a base housing 1 that contains a drive mechanism 2 with a rotary shaft 3 shown in broken lines. The drive mechanism 2, in particular a stepper motor, drives a disk-shaped rotary sample tray 4. The sample tray 4 has a plurality of holding accommodations 5 in the form of seating holes for sample beakers 32 arranged along a circular track on a circumference of the sample tray. The sample tray 4 has a handle 6, so that it can first be filled with samples 32 and then grasped by the handle 6 and set on the rotary shaft 3 that protrudes from the base housing 1. The rotary shaft 3 may enter, e.g., into a form-locking coupler opening below the handle 6 for a rotationally keyed engagement between the sample tray and the rotary shaft.

To simplify the drawing, only a part of the seating holes 5 in FIG. 1 are shown occupied by sample beakers 32. Instead of seating holes, it is also possible to hold the beakers 32 in clamping brackets arranged at the outside circumference of a tray disk 4 of smaller diameter. An open beaker 32a shown to the right of a tower 16 is identified as a conditioning or washing beaker by a magnet marker 30 (to be described later) that is placed in front of the beaker. In contrast to the beaker 32a, the beakers 32 shown to the left of the tower 16 are covered with a lid 32'. The lid 32' has several purposes: to protect operators from bad odors emanating from the samples; to prevent volatile solvents from escaping from the samples, which would falsify the analysis; and finally, to prevent foreign substances from getting into the samples without the intention of the operating personnel, which could likewise cause errors in the result of the analysis.

The sample tray 4 can have code markings at its underside, such as magnetic, optical, or other markings, e.g., to communicate to the analyzer system the type of analysis to be made on the samples 32 in the holding accommodations 5 and/or the movements to be performed by the drive mechanism 2. For example, it may be intended to analyze only the contents of every other beaker 32, while the beakers located in between are intended for a different program, e.g., a washing routine for analytical electrodes, or a conditioning routine. At least one stationary reader device is arranged on the topside of the base housing 1, for example at the location 7, to read the markings that are arranged on the sample tray 4, e.g., at the locations 8. The result of the reading is communicated to a controller module 9 which, in turn, sends commands to the drive mechanism 2 through a signal line 10 and/or transmits the reading through an internal signal line 11 and a connected external cable 11' to a controller instrument 12 that is preferably designed as a computer. The computer 12 can be used simultaneously to evaluate measurement data that are delivered to it by cables 13 (the latter shown only partially, without the measuring probes that they are connected to). However, it is preferred if at least the keypad 112 of the computer 12 is mounted directly on the base housing 1, as indicated symbolically by the broken lines 112', in order to keep the system as much as possible from becoming cluttered with cables.

In accordance with the aforementioned German patent application DE 100 18 876.1 which is hereby incorporated by reference in the present disclosure, the housing 1 has mounting holes spaced from each other at a distance corresponding either exactly to the distance between the holding accommodations 5 of the sample tray 4 or to a simple fraction of the distance, e.g., one half or one fourth. When an analyzer module configured as a tower 16 is fastened to the aforementioned mounting holes by means of fastening screws 17, a foot 18 of the tower 16 rests on the top surface of the base housing, while a vertical surface of the tower rests against the outside wall 14 of the base housing. This mounting arrangement ensures a stable installation of the tower 16 with only two mounting screws 17. A lid-opening device 50 for opening lids 32' that may be covering the sample beakers 32 is likewise installed by means of screws 17 (only one is shown in the drawing) in the aforementioned mounting holes at a location ahead of the tower 16 in relation to the rotary movement of the sample tray 4.

Of course, one could also use more than two mounting screws 17. Furthermore, the screws could be replaced by other types of fasteners, such as dowel pegs, pins, gripping hooks, etc. Also, a further horizontal mounting surface of the tower 16 or the lid-opening device 50 could reach below the bottom to the base housing 1, as the latter is in any event raised from the work surface of a laboratory counter (not shown), e.g., by adjustable feet 21.

A further advantage arises from the fact that each tower 16 can be equipped with its own reader device to direct the program or the sequence of motions of the sample tray 4 and to provide program commands to the tower 16 and the lid-opening device 50. The reader device, arranged at a location 28 on the lid-opening device 50 and/or the tower 16, can include, e.g., a Hall effect sensor, to sense the presence of magnets 30 that can be plugged into any of the receiving holes 29 associated with each of the sample-holding cutouts 5. This arrangement can be used, e.g., in combination with entering a corresponding instruction into the computer 12, to initiate a special program subroutine if a sample is marked by the presence of a plug-in magnet. For example, the special subroutine could be to exempt the marked samples from a pH-test and therefore advance those samples through the pH-testing tower without performing a pH measurement.

This arrangement could work, e.g., in such a manner that the sample tray 4 stops for the lid-opening device 50 to take a lid 32' off a sample beaker 32, if no marker 30 has been set for that particular beaker. If on the other hand a marker 30 were present at that beaker position, this would indicate that the beaker is a conditioning beaker 32a without a lid. In the case of a conditioning beaker 32a, the holder 22 at the tower 16 will not be lowered to perform an analysis. If it is lowered, it would only be for a conditioning or washing procedure. As is self-evident, the pick-up device 28 can be configured in any number of different ways, e.g., to pick up a line or color mark, or any other mark on the sample tray 4, instead of using a magnetic marker 30.

As is self-evident, the task is not finished after the lid 32' has been taken off the beaker 32. For the further handling of the lid 32', the lid-opening device could be designed to put the lid 32' on a transporting device such as, e.g., a conveyor belt that would move the lid 32' to a depository location for lids or to a lid-closing device downstream of the tower 16 in relation to the travel direction of the samples on the tray 4. However, the preferred concept in the case of the analyzer system of FIG. 1 is to design the lid-opening device 50 to also function as a lid-holding device that holds the lid 32' during the time period when the sample in the now open beaker 32 is analyzed at the tower 16. After the analysis has been completed, the lid 32' is put back on the beaker 32.

It will be understood that the lid-holding device could also be configured to be separate from the lid-opening device 50. For example, the lid-opening device could be designed as a gripping tool in the manner of a robot, which would deposit the lid 32' on a holding tray of the lid-holding device. After the analysis, the gripping tool would pick up the lid and set it back on the beaker 32. An analogous solution would also be conceivable with an electromagnet attached to a movable carrier. Obviously, the solutions just mentioned would require a complicated drive mechanism for the gripping tool or the movement of the magnet, which would be less economical than the preferred embodiment described above.

To allow the lid-opening device 50 to also function as a lid-closing device, the sample beaker 32 on the tray 4 has to be moved in a sequence of steps, first in a clockwise direction from the lid-opening device 50 (where the lid 32' has been removed) to the analyzer tower 16 (where the analysis is performed). After the analysis, the sample beaker is moved in the reverse direction back to the lid-opening/holding device, where the lid 32' (which has been held by the device 50 during the analysis) is set back on the beaker. To achieve greater clarity in the illustration of FIG. 1, the tower 16 is set apart from the lid-opening device 50 by two mounting holes 5 in the direction of the tray movement (clockwise), but it should be clear that the advancement of the beakers 32 through the analysis process will be speeded up if the lid-opening device 50 is as close as possible to the tower 16, i.e., only one step or one mounting hole 5 apart from the tower 16.

To synchronize the operations of the tray 4 and the lid-opening/holding device 50, the computer has signal lines 11' and 11" to the program-control unit 9 and the lid-opening/holding device, respectively. The program-control unit 9, by way of an electrical connection 10, controls the drive source, for example a stepper motor 2, for the sample tray, while the electromagnet (to be described in more detail in the context of FIG. 2) of the lid-opening/holding device 50 is controlled synchronously with the steps of the sample tray. The synchronized operations of the tray 4 and the lid-opening/holding device 50 may run according to the following program, except when a marker 30 calls for a deviation from the program:

1. The next sample beaker 32 in line is advanced clockwise to the lid-opening device 50 while, preferably, another, already opened sample beaker 32 is moved into position at the analyzer module 16.
2. The lid-opening magnet (to be described later) or another lid-opening actuator is energized while at the same time the holder 22 for the analytical instruments (electrodes, pipettes, etc.) is lowered into the beaker 32 that is positioned at the tower 16. The analysis is carried out, and the holder 22 is raised again, so that the instruments are retracted from the beaker 32. As an optional step, the instruments may also be washed at this time.
3. The sample beaker 32 that has been analyzed in step 2 is moved back (in counterclockwise direction) to the lid-opening/holding device 50 where the lid 32' has been held during the analysis.
4. The lid 32' is put back on the beaker containing the sample that was analyzed in step 2.
5. The cycle is repeated with the next following sample, starting again with step 1.

In a preferred program sequence, where the lid is kept off only during a minimum amount of time, the first series of sample beakers is preceded by a conditioning beaker 32*a* without a lid. The preferred program has these steps:

1. The first sample beaker is advanced clockwise to the lid-opening device 50 for removal of the lid 32'.
2. The sample tray 4 is moved counterclockwise until the conditioning beaker 32*a* is positioned at the lid-opening device 50. The lid 32' removed from the sample beaker in step 1 is put on the conditioning beaker 32*a*.
3. The sample tray 4 is advanced clockwise until the open sample beaker 32 is positioned at the tower 16, and the analysis is performed. As the tower 16 and the lid-opening device 50 are set only one step apart, the next following sample beaker 32 is now positioned at the lid-opening device 50.
4. The lid 32' is taken off and the sample tray 4 is rotated counterclockwise until the preceding sample beaker is positioned at the lid-opening device 50. The lid that has been held by the device is put on the preceding sample beaker.
5. The steps 3 and 4 are repeated until the series of sample beakers has been processed. In each subcycle 3–4, the lid of the new sample beaker is put on the preceding sample beaker. The series of sample beakers is followed at the end by a conditioning beaker 32*a* with a lid on, so that the last sample beaker in the series can likewise be closed with a lid after it has been analyzed.

Figure 2:
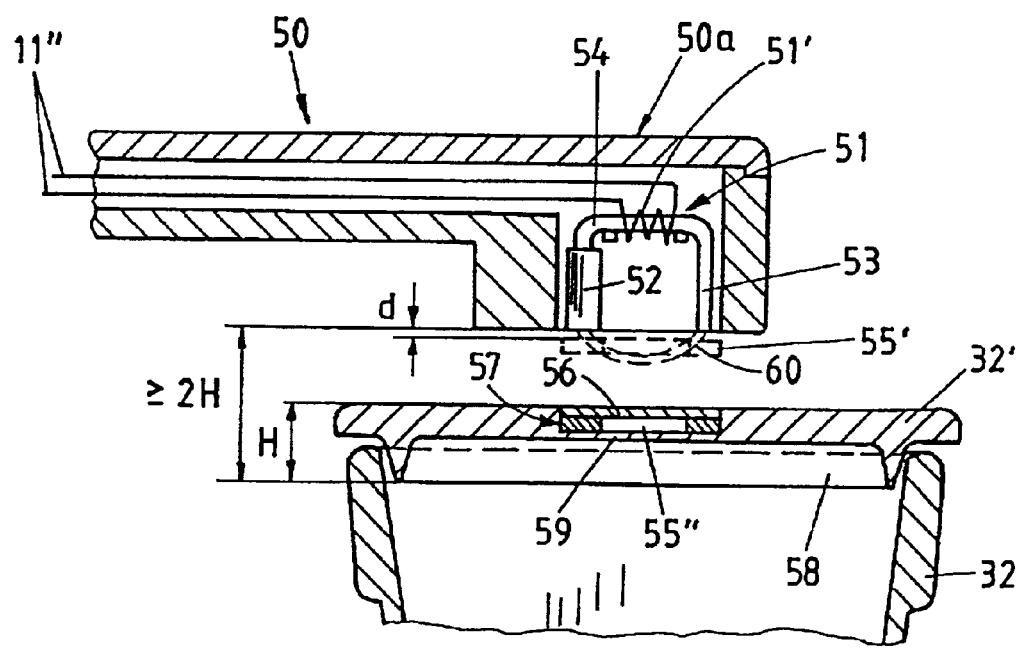
FIG. 2 represents a sectional view of the lid-opening device that is part of the analyzer system of FIG. 1.

FIG. 2 illustrates a preferred design of a lid-opening/holding device 50 with a particularly preferred embodiment of a lid 32'.

As may be seen in FIGS. 1 and 2, the lid-opening/holding device 50 has a substantially horizontal arm 50*a* reaching out over the sample beakers 32 on the sample tray 4. The arm 50*a* contains a lid-opening actuator that is preferably controlled by the computer 12 and/or the computer keypad 112 or 112'. In the preferred case, the lid-opening actuator is constituted by an electromagnet 51 that is connected to the computer by an electrical connection 11". An amplifier for the energizing current for the magnet can be accommodated at an arbitrary place, e.g., inside the housing of the computer 12. Thus, a coil 51' of the electromagnet 51 can be energized by the computer 12 by closing a switch S (FIG. 1) at a time that is prescribed by the program.

Given that, for practicality, the sample beakers 32 come up to a predetermined height from the seating cutouts 5 (i.e., only standardized sample beakers 32 are used), the lids 32' will likewise be of a known height H. As a practical design arrangement, a distance of at least 2H between the lid and the magnet should be chosen in order to allow the free passage of samples below the arm 50*a* even if two lids 32' are set on top of each other on a beaker 32 because of a malfunction or an operator error.

The electromagnet 51 can, in principle, be of an arbitrary shape, e.g., a bar magnet. However, it has been found that the magnetic hold on the lids will be more secure if the magnet 51 is configured with a yoke, i.e., a U-shaped core with poles 52 and 53 arranged approximately parallel at some distance from each other and facing towards the lid. It is advantageous if the yoke of the electromagnet 51 with the legs or poles 52 and 53 and the turn-around portion 54 has a "soft" magnetization characteristic, so that the remanent magnetization will be as small as possible.

An anchor element 55 in the lid 32' is positioned opposite the magnet 51. As a design choice, the preferably ring-shaped anchor element 55 may have a plastic cover layer 56 and may be pressed or snapped into a recess 57 of the lid 32'. The lid 32' is seated in a centered position on the sample beaker 32, preferably by means of a centering rim 58, to ensure a precisely centered alignment of the anchor element 55 with the magnet 51. While a centering rim of the kind illustrated in FIG. 2 is preferred, it is obvious that one could also use individual projections distributed over the circumference of the lid 32', or a circumferential groove that is engaged by the rim of the beaker. For an analogous reason, i.e., to assure the centered positioning of each seating cutout 5 under the magnet 51, it is preferable to use a stepper motor as a drive source for the movement of the sample tray 4, because a stepper motor provides a more precise positioning than other kinds of motors.

It is obvious that one could also choose to have more than one magnet-anchor element in the lid 32'. However, this would make the design of the lid-opening device somewhat more complex. In general, it will not be critical for the magnet-anchor element 55 to be exactly at the center of gravity of the lid 32'. However, with an offset anchor element, there could be malfunctions because the upward- and downward-directed forces acting on the lid are not in line with each other, so that the hold between the electromagnet and the magnet-anchor element is less secure. It is therefore preferred if the anchor element 55 is centered as much as possible.

In accordance with the advantageous embodiment described above, the anchor element 55 is covered from above by the plastic top layer 56 and from below by the bottom 59 of the recess 57. This has several advantages: On the one hand, aggressive vapors rising from the sample cannot corrode the metal of the anchor element 55 from below because the latter is protected by the bottom 59 of the recess. On the other hand, there is also protection from above, so that drops of an aggressive liquid falling on the lid 32' can likewise not corrode the anchor element. As a particularly preferred solution, rather than inserting the anchor element into a recess (as described above), the anchor element is completely molded into the lid 32', where the latter likewise consists of a non-magnetic material, particularly a polymer that is in general chemically inert.

In addition, the plastic layer 56 also serves as a spacer to ensure a minimum distance d from the magnet 51. This is necessary because with a safe distance of $\geq 2H$ between the lid and the magnet 51, the latter has to be designed to generate an attractive force strong enough to reach across the gap. However, with a strong magnet, there is a risk that even a small remanent magnetization may hold the lid 32' suspended in the position 55' indicated by a broken line, so that the lid cannot be placed back on the sample container after the analysis. Obviously, a spacer could also be realized in a different form, e.g., by upward projections of the lid that would bear against the underside of the arm 50a, but as explained above, the layer 56 of plastic material also serves other purposes.

The arrangement where the two poles 52, 53 lie opposite the anchor element 55 creates a closed magnetic circuit of flux lines 60 (shown in broken lines) which is conducive to a secure hold of the lid 32'. A ring-shaped anchor element 55 works particularly well, because in this case the flux pattern is independent of the orientation of the lid. It is of course advantageous if the ring diameter of the anchor element 55 corresponds approximately to the distance between the magnet poles 52, 53.

The design of the lid-opening device 50 with an electromagnet also has the advantage that there are no moving parts. As a result, the device has an uncomplicated layout and is assured to work without malfunction even if the switch S is closed in a situation when there is no lid on a sample beaker 32. Nevertheless, the closing of the switch could also be canceled, e.g., by the presence of a magnetic marker 30 causing the computer 12 to skip the switch closure step.

LIST OF REFERENCE NUMBERS 1 base housing
2 drive mechanism
3 shaft
4 sample tray
5 holding accommodation, seating hole
6 carrying handle
7 stationary reader device
8 markers
9 control device
10 electrical connection
11 internal electrical connection
11' cable
12 controller, computer
13 cable
14 outside wall of 1
16 analyzer module, tower
17 mounting screws
18 foot of 16
21 feet of 1
22 holder for analytical electrodes
28 reader device
30 magnet, plug-in marker
32 sample beaker
32' lid for sample beaker
32a conditioning beaker
50 lid-opening device
50a horizontal arm of 50
51 electromagnet
52, 53 magnet poles, legs of U-shaped core
54 turn-around portion, bottom of U
55 magnet-anchor element
56 layer of polymer material
57 recess
58 centering rim
59 bottom of 57
60 magnetic flux lines
112 keypad
112' keypad (alternative arrangement)

What is claimed is:

1. A laboratory analyzer system comprising a base housing (1); a sample tray (4) movably supported on the base housing; at least two holding accommodations (5) arranged on the sample tray (4) for holding a sample container (32) for a sample that is to be analyzed; a drive mechanism (2) arranged inside the base housing and operable to move the sample tray (4) so that the sample container (32) is advanced in a stepwise motion~ along a prescribed track; an analyzer module installed on the base housing along the prescribed track and operable to analyze the sample as it arrives at the analyzer module; and a lid-opening device (50) arranged along the prescribed track at a location that the sample container (32) reaches before it arrives at the analyzer module (16), said lid-opening device (50) being operable to open a lid (32') by which the sample container (32) may be covered, said lid (32') having a predetermined shape and thickness (H), wherein the lid-opening device (50) comprises an electromagnet (51) energizable through a switch (S) and configured to hold the lid (32') in an open position.

2. The analyzer system of claim 1, wherein the electromagnet (51) comprises a U-shaped core (52, 53, 54) with poles (52, 53) facing the lid (32').

3. The analyzer system of claim 2, wherein the lid (32') has a thickness (H) and the electromagnet (51) is installed in a stationary condition in the lid-opening device (50) at a distance from the lid (32') corresponding to at least twice the thickness (H).

4. The analyzer system of claim 1, wherein the lid-opening device (50) is adapted to be installed on the base housing (1) by means of a non-destructively releasable mounting arrangement (17) consisting of at least two parts.

5. The analyzer system of claim 1, wherein the drive mechanism (2) is a rotary drive mechanism and the sample tray (4) is disk-shaped and driven in rotary movement by the rotary drive mechanism.

6. The analyzer system of claim 5, wherein the holding accommodations (50) are positioned along a circle at equal angular intervals and the lid-opening device (50) is offset from the analyzer module (16) by only one of said angular intervals.

7. The analyzer system of claim 1, wherein the analyzer module (16) is adapted to cooperate with a control arrangement comprising at least one program to control the movements of the analyzer system, said at least one program having steps by which
   a) the lid-opening device (50) can be actuated to remove and hold the lid (32'),
   b) the sample container (32) is advanced to the analyzer module (16), so that an analysis can be performed,
   c) the sample container (32) is returned to the lid-opening device (50) and the lid (32') is set back on the sample container (32), d) a next following sample container is advanced to the lid-opening device (50).

8. The analyzer system of claim 1, wherein the analyzer module (16) is adapted to cooperate with a control arrangement comprising at least one program to control the movements of the analyzer system, said at least one program having steps by which a) the lid-opening device (50) can be actuated to remove the lid (32') from the sample container (32), b) an immediately preceding sample container is returned from the analyzer module (16) to the lid-opening device (50) and the lid (32') held from step a) is placed on said preceding sample container, c) the sample tray (4) is advanced so that the sample container (32) is moved to the analyzer module (16) for an analysis to be performed, while at the same time a next following sample container is advanced to the lid-opening device (50)

9. The analyzer system of claim 1, wherein the analyzer module (16) is adapted to cooperate with a control arrangement comprising at least one program to control the movements of the analyzer system, and further comprising at least one sensor mark (8, 30) on the sample tray (4) and a stationary reader device (7, 28) for the sensor mark (8, 30), said reader device being located on at least one of the base housing (1), the analyzer module (16), and the lid-opening device (50), said at least one sensor mark (8, 30) and said reader device (7, 28) being operable to control at least one of the sample tray (4) and the lid-opening device (50).

10. The analyzer system of claim 9, wherein the sensor mark (30) is designed for non-destructively releasable attachment to the sample tray (4) through a fastening arrangement (29) adjacent to at least one of the holding accommodations (5).

11. The analyzer system of claim 1, wherein the analyzer module (16) is adapted to cooperate with a control arrangement comprising at least one program to control the movements of the analyzer system, and wherein further the control arrangement is adapted to cooperate with a keypad (112, 112').

12. The analyzer system of claim 11, wherein the keypad (112') is connected to the base housing (1).

13. The analyzer system of claim 2, wherein the lid (32') is made of a non-magnetic material containing a magnet-anchor element (55).

14. The analyzer system of claim 13, wherein the magnet-anchor element (55) is covered by a layer (56) the non-magnetic material, said layer defining a prescribed distance (d).

15. The analyzer system of claim 14, wherein the magnet-anchor element (55) is completely encased in the non-magnetic material.

16. The analyzer system of claim 15, wherein the non-magnetic material is a polymer material and the magnet-anchor element is molded into the polymer material.

17. The analyzer system of claim 13, wherein the magnet-anchor element is ring-shaped, substantially as wide as the electromagnet (51) is from one pole to the other, and approximately centered in the lid (32').

18. The analyzer system of claim 13, wherein the lid (32') comprises at least one of a centering projection (58) and a centering recess for centering the lid (32') on the sample container (32).

* * * * *